(12) United States Patent
Akagane

(10) Patent No.: US 10,328,288 B2
(45) Date of Patent: Jun. 25, 2019

(54) VIBRATION TRANSMITTING UNIT AND ULTRASONIC TREATMENT INSTRUMENT

(71) Applicant: OLYMPUS CORPORATION, Hachioji-shi, Tokyo (JP)

(72) Inventor: Tsunetaka Akagane, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 15 days.

(21) Appl. No.: 15/622,443

(22) Filed: Jun. 14, 2017

(65) Prior Publication Data

US 2017/0274226 A1 Sep. 28, 2017

Related U.S. Application Data

(63) Continuation of application No. PCT/JP2016/054121, filed on Feb. 12, 2016.

(30) Foreign Application Priority Data

Mar. 17, 2015 (JP) .................................. 2015-053929

(51) Int. Cl.
*A61B 18/00* (2006.01)
*A61N 7/02* (2006.01)
(Continued)

(52) U.S. Cl.
CPC ........ *A61N 7/02* (2013.01); *A61B 17/320068* (2013.01); *A61B 18/00* (2013.01);
(Continued)

(58) Field of Classification Search
CPC .. A61B 2017/22015; A61B 17/320068; A61B 2017/320089; A61B 2017/32009; A61N 7/00; A61F 9/00745; H01L 41/22
(Continued)

(56) References Cited

U.S. PATENT DOCUMENTS 5,380,274 A   1/1995 Nita
5,427,118 A * 6/1995 Nita .................. A61B 17/22012
                                                   600/585
(Continued)

FOREIGN PATENT DOCUMENTS

EP        2074955 B1    7/2013
JP    H02-098346 A      4/1990
(Continued)

OTHER PUBLICATIONS

Apr. 26, 2016 Written Opinion issued in Patent Application No. PCT/JP2016/054121.
(Continued)

*Primary Examiner* — Diane D Yabut
*Assistant Examiner* — Socrates L Boutsikaris
(74) *Attorney, Agent, or Firm* — Oliff PLC

(57) ABSTRACT

An extending portion of a vibration transmitting unit. is capable of transmitting ultrasonic vibration from a proximal side to a distal side, and in the extending portion, a second component provided on the distal side with respect to a first component. A third component provided between the first component and the second component in the extending portion has a third cross-sectional area that is larger than a first cross-sectional area of the first component and is smaller than a second cross-sectional area of the second component, and one of vibration anti-nodes is positioned at third component by the extending portion vibrating at a frequency in a predetermined frequency range.

20 Claims, 5 Drawing Sheets

(51) Int. Cl.
  *A61B 17/32* (2006.01)
  *A61B 18/08* (2006.01)
  *A61B 18/10* (2006.01)
  *A61B 17/00* (2006.01)
  *A61N 7/00* (2006.01)
  *A61B 17/22* (2006.01)

(52) U.S. Cl.
  CPC ............ *A61B 18/085* (2013.01); *A61B 18/10* (2013.01); *A61B 2017/00402* (2013.01); *A61B 2017/22018* (2013.01); *A61B 2017/320089* (2017.08); *A61B 2018/00607* (2013.01); *A61B 2018/00702* (2013.01); *A61B 2018/00922* (2013.01); *A61B 2018/00952* (2013.01); *A61B 2018/00988* (2013.01); *A61N 2007/0091* (2013.01)

(58) Field of Classification Search
  USPC ............... 606/169; 310/323.12, 323.13, 311; 601/2; 604/22
  See application file for complete search history.

(56) References Cited

U.S. PATENT DOCUMENTS

| | | | |
|---|---|---|---|
| 2006/0090956 A1 | 5/2006 | Peshkovskiy et al. | |
| 2007/0173871 A1* | 7/2007 | Houser | A61B 17/320092 606/169 |
| 2009/0030437 A1* | 1/2009 | Houser | A61B 17/320092 606/169 |
| 2011/0040212 A1 | 2/2011 | Dietz et al. | |
| 2013/0116717 A1 | 5/2013 | Balek et al. | |
| 2015/0080927 A1 | 3/2015 | Akagane | |

FOREIGN PATENT DOCUMENTS

| | | |
|---|---|---|
| JP | 2003-190180 A | 7/2003 |
| WO | 2007/047531 A2 | 4/2007 |
| WO | 2007/084731 A2 | 7/2007 |
| WO | 2007/143439 A2 | 12/2007 |
| WO | 2011/020097 A2 | 2/2011 |
| WO | 2012/149361 A1 | 11/2012 |
| WO | 2014/038273 A1 | 3/2014 |

OTHER PUBLICATIONS

Nov. 8, 2016 Office Action issued in Japanese Patent Application No. 2016-546855.
Apr. 26, 2016 International Search Report issued in Patent Application No. PCT/JP2016/054121.
May 30, 2018 Extended European Search Report issued in European Patent Application No. 16764600.9.

* cited by examiner

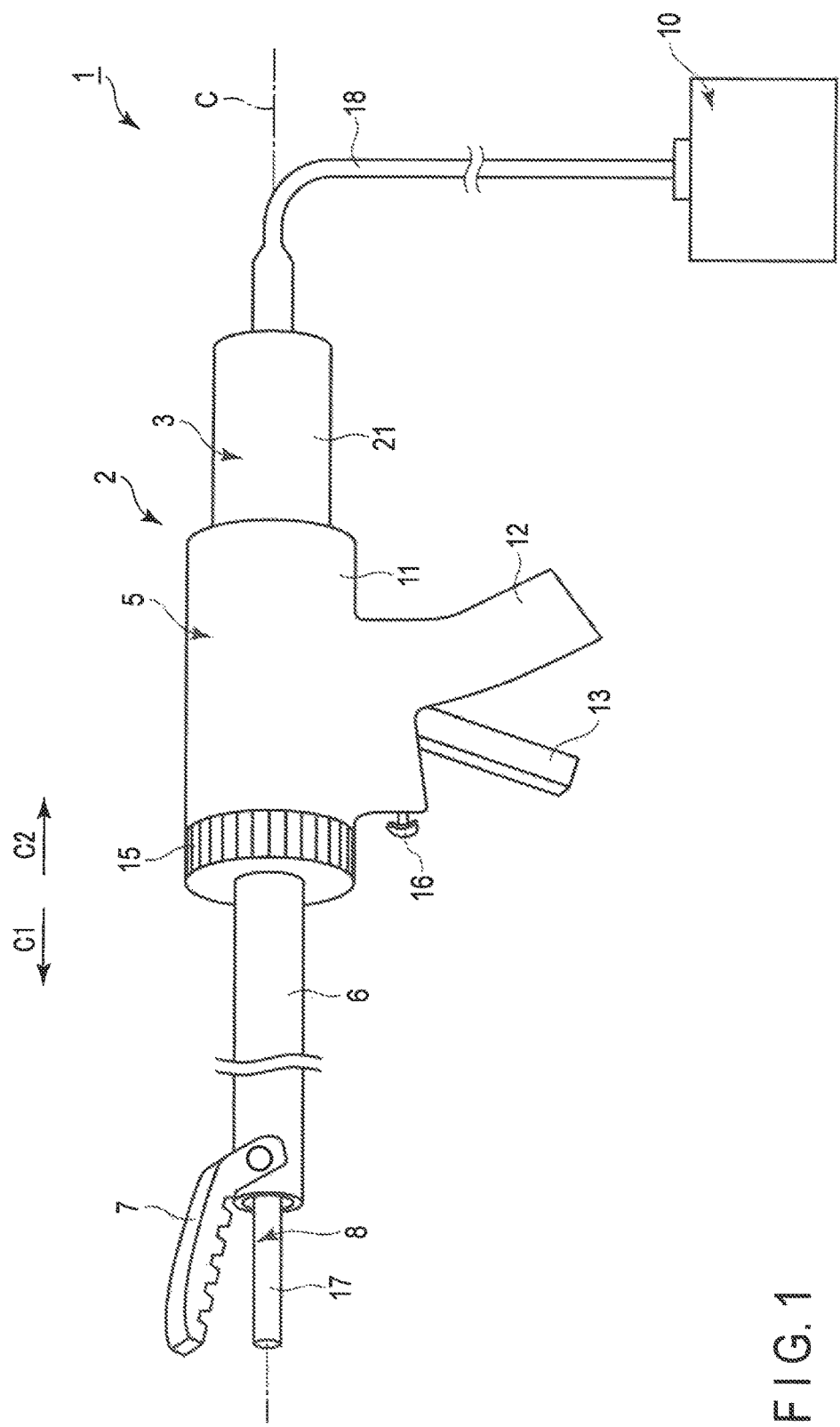
F I G. 1

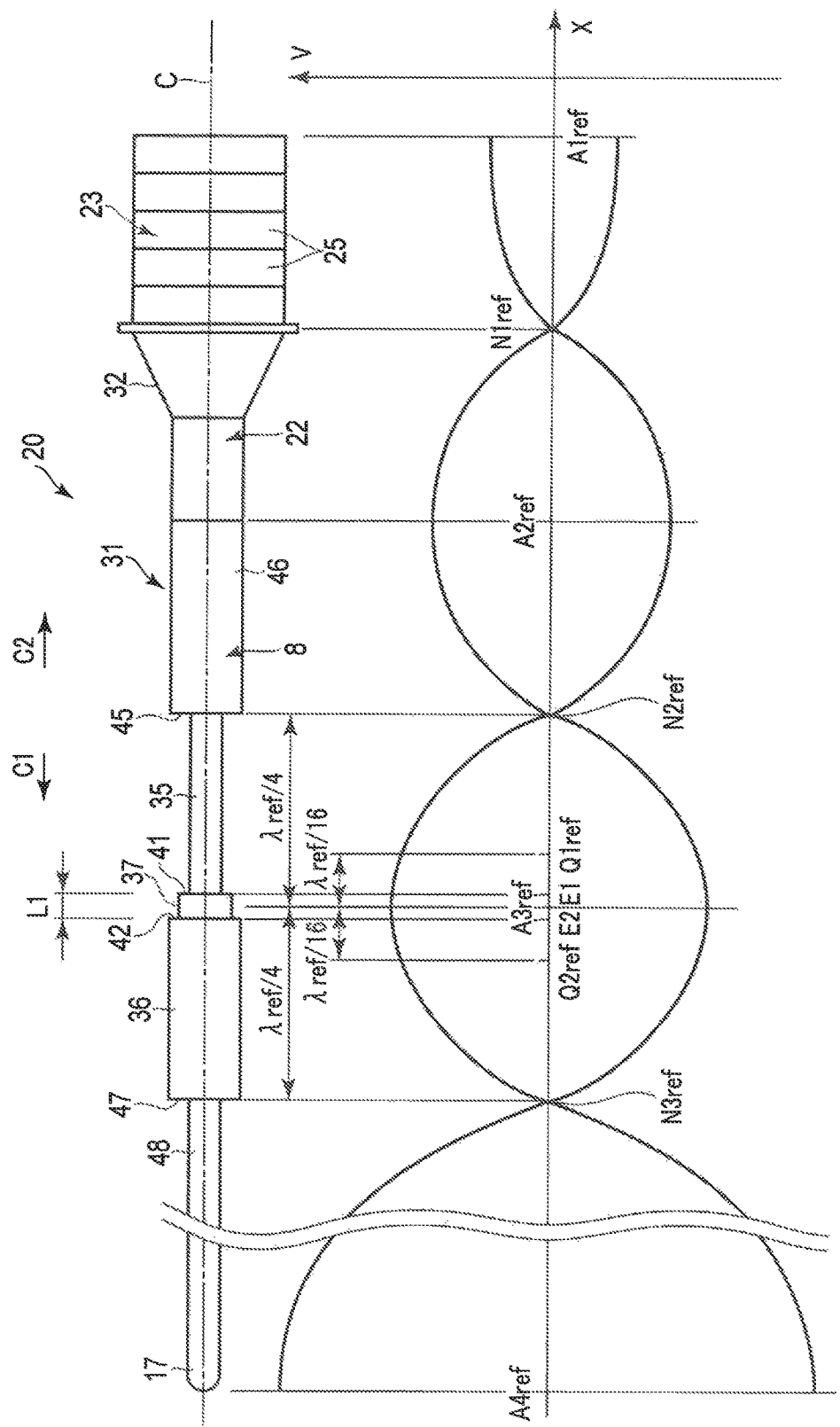
F I G. 3

VIBRATION TRANSMITTING UNIT AND ULTRASONIC TREATMENT INSTRUMENT

CROSS-REFERENCE TO RELATED APPLICATIONS

This is a Continuation Application of PCT Application No. PCT/JP2016/054121, filed Feb. 12, 2016 and based upon and claiming the benefit of priority from prior Japanese Patent Application No. 2015-053929, filed Mar. 17, 2015, the entire contents of which are incorporated herein by reference.

BACKGROUND OF THE INVENTION

1. Field of the Invention

The present invention relates to a vibration transmitting unit that enables ultrasonic vibration to be transmitted, and an ultrasonic treatment instrument including the vibration transmitting unit.

2. Description of the Related Art

European Patent No. 2074955 specification discloses an ultrasonic treatment instrument including a vibration transmitting unit which is designed so as to vibrate at a standard resonance frequency by an ultrasonic vibration transmitted from a proximal side to a distal side. This vibration transmitting unit is provided with a plurality of cross-sectional reduction portions at which a cross-sectional area perpendicular to a longitudinal axis decreases towards the distal side. In a state where the vibration transmitting unit vibrates at the standard resonance frequency, all of the vibration anti-nodes are positioned away from each of the cross-sectional reduction portions in a direction parallel to the longitudinal axis. Therefore, stress caused by vibration acts on each of the plurality of cross-sectional reduction portions, thereby increasing the amplitude of the vibration. Furthermore, in the vibration transmitting unit, a cross-sectional increasing portion, at which a cross-sectional area perpendicular to the longitudinal axis increases towards the distal side, is provided between two cross-sectional reduction portions in a direction parallel to the longitudinal axis in a state where the vibration transmitting unit vibrates at the standard resonance frequency, one of the vibration anti-nodes is positioned at the cross-sectional increasing portion. Since a vibration anti-node in which stress caused by vibration becomes zero is positioned, the amplitude of the vibration does not decrease even at the cross-sectional increasing portion at which the cross-sectional area increases.

BRIEF SUMMARY OF THE INVENTION

According to one aspect of the invention, a vibration transmitting unit including: an extending portion which extends along a longitudinal axis, and which is capable of transmitting ultrasonic vibration from a proximal side to a side; a first component which is provided in the extending portion, and which has a first cross-sectional area in a cross-section perpendicular to the longitudinal axis; a second component which is provided on the distal side with respect to the first component in the extending portion, and which has a second cross-sectional area, which is larger than the first cross-sectional area, in a cross-section perpendicular to the longitudinal axis; and a third component which is provided between the first component and the second component in the extending portion, and which has a third cross-sectional area, which is larger than the first cross-sectional area and is smaller than the second cross-sectional area, in a cross-section perpendicular to the longitudinal axis, a standard vibration anti-node, which is one of vibration anti-nodes, being positioned at the third component by the ultrasonic vibration causing the extending portion to vibrate at a frequency in a predetermined frequency range.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 1 is a schematic view showing an ultrasonic system according to a first embodiment, FIG. 3 is a schematic view showing a configuration of a vibration transmitting unit and an ultrasonic transducer according to the first embodiment, and, in a state where the vibration transmitting unit performs longitudinal vibration at a standard resonance frequency, showing a relationship between a position in a direction along a longitudinal axis and an amplitude of the longitudinal vibration.

Figure 2:
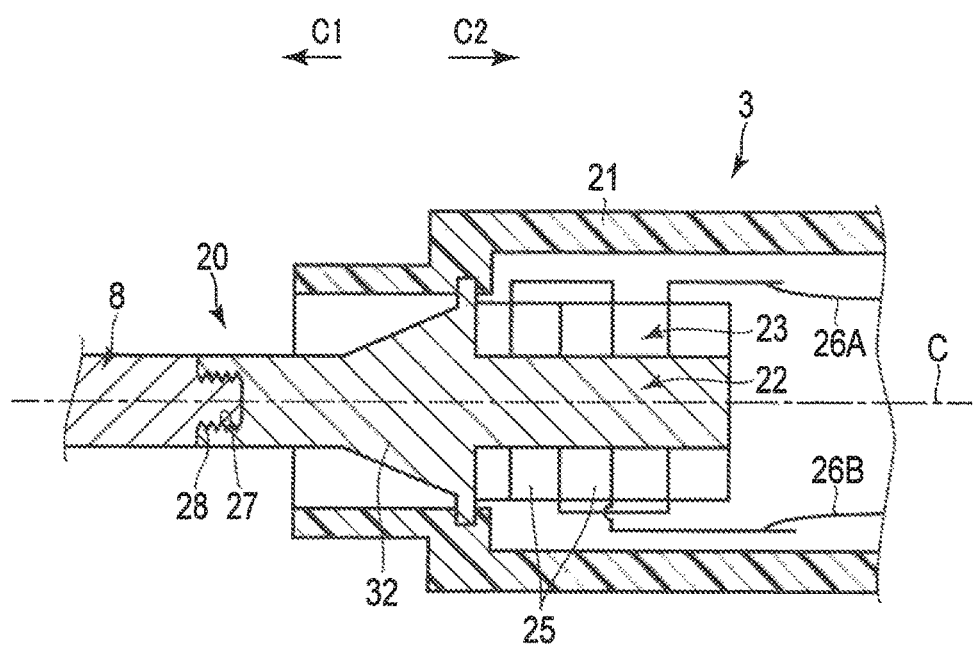
FIG. 2 is a cross-sectional view schematically showing a transducer unit according to the first embodiment.

DETAILED DESCRIPTION OF THE INVENTION (First Embodiment)

The first embodiment of the present invention will be explained with reference to FIGS. 1 to 4.

FIG. 1 shows an ultrasonic treatment system 1 according to the present embodiment. As shown in FIG. 1, the ultrasonic treatment system 1 includes an ultrasonic treatment instrument 2. The ultrasonic treatment instrument 2 has a longitudinal axis C. Here, one side of a direction parallel to the longitudinal axis C (a longitudinal axis direction) is a distal side (a side of an arrow C1 in FIG. 1), and a side opposite to the distal side is a proximal side (a side of an arrow C2 in FIG. 1).

The ultrasonic treatment instrument 2 includes a transducer unit 3, a held unit 5 which can be held by an operator, etc., a sheath 6, a jaw (grasp member) and a distal side transmitting member (probe) 8. The held unit 5 includes a held body portion 11 extending along the longitudinal axis C, a stationary handle 12 extending from the held body portion 11 towards a certain direction intersecting the longitudinal axis C, and a movable handle 13 rotatably attached to the held body portion 11. When the movable handle 13 is rotated with respect to the held body portion 11, the movable handle 13 is closed or open with respect to the stationary handle 12. A rotating operation knob 15, which is a rotating operation input portion, is connected to the distal side of the held body portion 11. The rotating operation knob 15 is rotatable about the longitudinal axis C with respect to the held body portion 11. An energy operation button 16, which is an energy operation input portion, is attached to the held body portion 11.

The sheath 6 is coupled to the held unit 5 in a state where it is inserted from the distal side into the turning operation knob 15 and the held body portion 11. The jaw 7 is rotatably attached to a distal portion of the sheath 6. The distal side transmitting member 8 extends towards the distal side from the inside of the held body portion 11 through the inside of the sheath 6. In the present embodiment, the central axis of the distal side transmitting member 8 coincides with the longitudinal axis C, and the distal side transmitting member 8 extends along the longitudinal axis C. A treatment portion 17 is provided in the distal portion of the distal side transmitting member 8. The distal side transmitting member 8 is inserted through the sheath 6 in a state where the treatment portion 17 protrudes from the distal end of the sheath towards the distal side. When the movable handle 13, which is an opening/closing operation input portion, performs an opening motion or a closing motion with respect to the stationary handle 12, the movable portion (not shown) of the sheath 6 moves along the longitudinal axis C, and the law 7 is rotated. When the law 7 is rotated, it performs an opening motion or a closing motion with respect to the treatment portion 17 of the distal side transmitting member 8. The sheath 6, the law 7, and the distal side transmitting member 8 are integrally rotatable with the turning operation knob 15 about the longitudinal axis C with respect to the held body portion 11.

FIG. 2 shows a configuration of the transducer unit 3. As shown in FIGS. 1 and 2, the transducer unit 3 includes a transducer case 21 which forms the exterior of the transducer unit 3. The transducer case 21 is coupled to the held unit 5 in a state where it is inserted from the proximal side into the held body portion 11. Inside the held body portion 11, the transducer case 21 is separably connected to the sheath 6. One end of a cable 18 is connected to the transducer case 21. In the ultrasonic treatment system 1, the other end of the cable 18 is separably connected to an energy source unit 10. Here, the energy source unit 10 is, for example, an energy control device for medical use, and includes an electric power source and a conversion circuit which converts electric power from the electric power source into electric power that generates ultrasonic vibration. The energy source unit 10 has a processor including a Central Processing Unit (CPU) or an Application Specific Integrated Circuit (ASIC), etc. and a storage (not shown), such as a memory.

Inside the transducer case 21, a proximal side transmitting member (a horn member) extends along the longitudinal axis C. The proximal side transmitting member 22 is attached to the transducer case 21. An ultrasonic transducer 23 which is a vibration generator is attached to the proximal side transmitting member 22. The Ultrasonic transducer 23 includes piezoelectric elements 25 configured to convert a current into ultrasonic vibration. The ultrasonic transducer 23 is connected to one end of electrical wirings 26A and 26B. The electrical wirings 26A and 26B extend through the inside of the cable 18 and have the other ends connected to the energy source unit 10. Inside the held unit 5, a switch (not shown) is provided. The switch is switched between an open/closed state corresponding to the input of an energy operation by the energy operation button 16. The switch is connected to the energy source unit 10 via an electric signal line (not shown).

By detecting the open/closed state of the switch, the processor of the energy source unit 10 detects that an energy operation has been input by the energy operation button 16. By detecting the energy operation input, an electric power to generate ultrasonic vibration is output from the energy source unit 10. The electric power (vibration generating electrical energy) output from the energy source unit 10 is supplied to the ultrasonic transducer 23 via the electrical wirings 26A and 26B. This causes the ultrasonic vibration to be generated in the ultrasonic transducer 23.

A female screw portion 27 is formed at the distal end of the proximal side transmitting member 22, and, a male screw portion 28 is formed at the proximal end of the distal side transmitting member 8. As the female screw portion 27 and the male screw portion 28 are screwed together, the distal side transmitting member 8 is connected to the distal side of the proximal side transmitting member 22. The distal side transmitting member 8 is connected to the proximal side transmitting member 22 inside the held body portion 11. By connecting the distal side transmitting member 8 to the proximal side transmitting member 22, a vibration transmitting unit 20 is formed. The ultrasonic vibration generated in the ultrasonic transducer 23 is transmitted to the vibration transmitting unit 20.

FIG. 3 shows a configuration of the vibration transmitting unit 20 and the ultrasonic transducer 23. As shown in FIG. 3, in the vibration transmitting unit 20, an extending portion 31 extends along the longitudinal axis C. The ultrasonic vibration transmitted to the vibration transmitting unit 20 is transmitted from the proximal side to the distal side in the extending portion 31. The ultrasonic vibration is transmitted to the treatment portion 17 of the distal side transmitting member 8, and the treatment portion 17 uses the transmitted ultrasonic vibration to treat a treated target of a living tissue, etc. The proximal side transmitting member 22 and the distal side transmitting member 8 are formed by a material with high vibration transmissibility, such as 64 titanium (Ti-6Al-4V) or duralumin.

In the vibration transmitting unit 20 (extending portion 31), a cross-sectional reduction portion (horn cross-sectional reduction portion) 32 is provided in the proximal side transmitting member 22. In the cross-sectional reduction portion 32, a cross-sectional area perpendicular to the longitudinal axis C as reduced towards the distal side. In the present embodiment, the cross-sectional reduction portion 32 is formed in a tapered shape.

In the vibration transmitting unit 20 (extending portion 31), a first component 35 and a second component 36 are provided in the distal side transmitting member 8. The second component 36 is positioned on the distal side with respect to the first component 35. The first component 35 has a first cross-sectional area S1 (not shown) in the cross-section perpendicular to the longitudinal axis C. The second component 36 has a second cross-sectional area S2 (not shown) in the cross-section perpendicular to the longitudinal axis C. The second cross-sectional area S2 of the second component 36 is larger than the first cross-sectional area S1 of the first component 35.

In the extending portion 31 of the vibration transmitting unit 20, a third component 37 extends between the first component 35 and the second component 36 in a direction parallel to the longitudinal axis C (a direction along the longitudinal axis C). The third component 37 has a third cross-sectional area S3 (not shown) in the cross-section perpendicular to the longitudinal axis C. The third cross-sectional area 33 of the third component 37 is larger than the first cross-sectional area S1 of the first component 35 and is smaller than the second cross-sectional area S2 of the second component 36. Accordingly, a cross-sectional increasing portion (proximal side cross-sectional increasing portion) 41, which increases the cross-sectional area perpendicular to the longitudinal axis C from the first cross-sectional area S1 to the third cross-sectional area S3 towards the distal side, is formed between the first component 35 and the third component 37. A cross-sectional increasing portion (distal side cross-sectional increasing portion) 42, which increases the cross-sectional area perpendicular to the longitudinal axis C from the third cross-sectional area S3 to the second cross-sectional area S2 towards the distal side, is formed between the third component 37 and the second component 36. in the present embodiment, the cross-sectional increasing portions 41 and 42 are formed stepwise. It is preferable that. the third cross-sectional area S3 is same as an average value of the first cross-sectional area S1 and the second cross-sectional area S2. That is, preferably, the following formula (1) should be satisfied.

[Formula 1]

$$S3=(S1+S2)/2 \qquad (1)$$

The third component 37 has an extending dimension L1 in a direction parallel to the longitudinal axis C. In the present embodiment, the proximal end of the third component 37 is continuous with a distal end E1 of the first component. 35, and the distal end of the third component 37 is continuous with a proximal end E2 of the second component 36.

The distal side transmitting member 8 of the vibration. transmitting unit 20 (extending portion 31) includes a cross-sectional reduction portion (proximal side cross-sectional reduction portion) 45. The cross-sectional reduction portion (first cross-sectional reduction portion.) 45 is positioned on the proximal side with respect to the first component 35. In the extending portion 31 of the vibration transmitting unit 20, a relay portion (proximal 1) side relay portion) 46 extends between the cross-sectional reduction portion 32 and cross-sectional reduction portion 45 in a direction parallel to the longitudinal axis C. The relay portion (first relay portion) 46 has a cross-sectional area (relay portion cross-sectional area) S4 (not shown) in the cross-section perpendicular to the longitudinal axis C. The cross-sectional area S4 of the relay portion 46 is larger than the first cross-sectional area S1 of the First component 35. Accordingly, at the cross-sectional reduction portion 45, a cross-sectional area perpendicular to the longitudinal axis C is reduced from the cross-sectional area S4 to the first cross-sectional area Si towards the distal side. In the present embodiment, the cross-sectional reduction portion 45 is formed stepwise.

The distal side transmitting member 8 of the vibration transmitting unit 20 (extending portion 31) includes a cross-sectional reduction portion (distal side cross-sectional reduction portion) 47. The cross-sectional reduction portion (second cross-sectional reduction portion) 47 is positioned on the distal side with respect to the second component 36. In the extending portion 31 of the vibration transmitting unit 20, a relay portion (distal side relay portion) 48 extends between the cross-sectional reduction portion 47 and the treatment portion 17 in a direction parallel to the longitudinal axis C. The relay portion (second relay portion) 48 has a cross-sectional 1) area (relay portion cross-sectional area) S5 (not shown) in the cross-section perpendicular to the longitudinal axis C. The cross-sectional area S5 of the relay portion 48 is smaller than the second cross-sectional area S2 of the second component 36. Accordingly, at the cross-sectional reduction portion 47, a cross-sectional area perpendicular to the longitudinal axis C is reduced from the second cross-sectional area S2 to the cross-sectional area S5 towards the distal side. In the present embodiment, the cross-sectional reduction portion 47 is formed stepwise.

In the case where the cross-section of the first to the third components 35, 36, and 37 and the relay portions 46 and 48 perpendicular to the longitudinal axis C are in circular shapes, the longitudinal axis C passes through each center of the first cross-sectional area S1 of the first component 35, the second cross-sectional area S2 of the second component 36, the third cross-sectional area S3 of the third component 37, the cross-sectional area S4 of the relay portion 46, and the cross-sectional area 35 of the relay portion 48.

Next, the function and advantages of the vibration transmitting unit 20 and the ultrasonic treatment instrument 2 of the present embodiment will be explained. When using the ultrasonic treatment instrument 2 to perform a treatment, the sheath 6, the jaw 7, and the distal side transmitting member 8 are inserted into the body in a state where the held unit 5 is held. The treated target such as the living tissue is arranged between the jaw 7 and the treatment portion 17 of the distal side transmitting member 8. In this state, the closing motion of the movable handle 13 with respect to the stationary handle 12 is performed to close the jaw 7 with respect to the treatment portion 17 so that the treated target is grasped between the law 7 and the treatment portion 17. By inputting the energy operation by the energy operation button 16 in the state where the treated target is grasped, an electric power (electric energy) to generate ultrasonic vibration is supplied to the ultrasonic transducer 23 from the energy source unit 10. Thus, the ultrasonic vibration is generated in the ultrasonic transducer 23 (piezoelectric elements 25). The generated ultrasonic vibration is transmitted from the proximal side to the distal side towards the treatment portion 17 in the vibration transmitting unit 20. In the present embodiment, this allows the vibration transmitting unit 20 to perform longitudinal vibration in which the vibration direction is in parallel to the longitudinal axis C. The treatment portion 17 performing longitudinal vibration in a state where the treated target is grasped between the jaw 7 and the treatment portion 17 causes frictional heat to be generated between the treatment portion 17 and the treated target. The frictional heat causes coagulation and incision of the treated target at the same time.

The vibration transmitting unit 20 is designed so as to vibrate (longitudinal vibrate) at a standard resonance frequency Frref (for example, 47 kHz) by transmitting the ultrasonic vibration generated in the ultrasonic transducer 23 from the proximal side to the distal side. Here, in the process of manufacturing, variability may occur in the physical properties (Young's modulus, in particular) of materials for each part of the proximal side transmitting member 22 and the distal side transmitting member 8 that form the vibration transmitting unit 20. For example, when variability occurs in the physical properties of materials with respect to each distal side transmitting member 8 that is manufactured, in the vibration transmitting unit 20, the resonance frequency Fr in a vibrating state changes corresponding to the physical properties of the materials of the distal side transmitting member 8 connected to the proximal side transmitting member 22. When heat generated upon treatment in the treatment portion 17 causes the temperature of the treatment portion 17 to increase, the resonance frequency Fr of the vibration transmitting unit 20 also changes.

That is, the vibration transmitting unit 20 does not always vibrate at the standard resonance frequency Frref since the resonance frequency Fr in a state of vibration by the ultrasonic vibration varies according to the physical properties of the materials forming the vibration transmitting unit 20 and the heated state in the treatment portion 17. Accordingly, based on the ultrasonic vibration generated at the ultrasonic transducer 23, the vibration transmitting unit 20 vibrates (longitudinal vibrates) at a frequency in a predetermined frequency range $\Delta f$ between a minimum resonance frequency Frmin (for example, 46 kHz) and a maximum resonance frequency Frmax (for example, 48 kHz). The standard resonance frequency Frref is included in the predetermined frequency range $\Delta f$. As mentioned above, dimensions, etc. of the vibration transmitting unit 20 is determined so as to vibrate at a frequency in the predetermined frequency range $\Delta f$ including the standard resonance frequency Frref by transmitting the ultrasonic vibration generated at the ultrasonic transducer 23. The frequency, etc. of a current (alternating current) to be supplied to the ultrasonic transducer 23 (piezoelectric elements 25) is also adjusted so that the vibration transmitting unit 20 vibrates at a frequency in the predetermined frequency range $\Delta f$ including the standard resonance frequency Frref.

FIG. 3 is a graph showing the relationship between a position in the direction along the longitudinal axis C and an amplitude of the longitudinal vibration in a state where the vibration transmitting unit 20 performs the longitudinal vibration at the standard resonance frequency Frref as a frequency in the frequency range $\Delta f$. In this graph, a position (X) in the direction along the longitudinal axis C is shown on the abscissa axis, and an amplitude of the longitudinal vibration (V) is shown on the ordinate axis. In a state where the vibration transmitting unit 20 is performing the longitudinal vibration, the distal end and the proximal end of the vibration transmitting unit 20 become free ends. Therefore, one of the vibration anti-nodes of the vibration (longitudinal vibration) is positioned at the proximal end of the vibration transmitting unit 20 (proximal end of the proximal side transmitting member 22), and one of the vibration anti-nodes of the ultrasonic vibration is positioned at the distal end of the vibration transmitting unit 20 (distal end of the distal side transmitting member 8). As shown in FIG. 3, in a state where the vibration. transmitting unit 20 performs longitudinal vibration at the standard resonance frequency Frref, vibration anti-node A1 (shown as A1ref in FIG. 3), which is one of the vibration anti-nodes of the longitudinal vibration, is positioned at the proximal end of the vibration transmitting unit 20, and a vibration anti-node A4 (shown as A4ref in FIG. 3, which is one of the vibration anti-nodes of the longitudinal vibration, is positioned at the distal end of the vibration. transmitting unit 20. In the present embodiment, the vibration anti-node A1 is positioned most proximally among the vibration anti-nodes of the longitudinal vibration, and the vibration anti-node A4 is positioned most distally among the vibration anti-nodes of the longitudinal vibration.

In a state where the vibration transmitting unit 20 vibrates at the standard resonance frequency Frref, a vibration node N1 (shown as N1ref in FIG. 3), which is one of the vibration nodes of the longitudinal vibration, is positioned at the proximal end (input end) of the cross-sectional reduction portion 32. In a state where the vibration transmitting unit 20 performs longitudinal vibration at a frequency in the predetermined frequency range $\Delta f$ (between Frmin and Frmax), the vibration node NI is positioned at the proximal end of the cross-sectional reduction portion 32, or in the vicinity thereof. Therefore, in a state where the vibration transmitting unit 20 performs longitudinal vibration at a frequency in the predetermined frequency range $\Delta f$, all of the vibration anti-nodes A1 to A4 of the longitudinal vibration are positioned away from the cross-sectional reduction portion 32 in the direction parallel to the longitudinal axis C. Since vibration anti-nodes A1 to A4 at which stress caused by vibration becomes zero are not positioned at the cross-sectional reduction portion 32, stress caused by vibration acts on the cross-sectional reduction portion 32 at which the cross-sectional area perpendicular to the longitudinal axis C decreases towards the distal side. Accordingly, the cross-sectional reduction portion 32 increases the amplitude of the longitudinal vibration.

In a state where the vibration transmitting unit 20 vibrates at the standard resonance frequency Frref, the vibration anti-node A2 (shown as A2ref in FIG. 3), which is one of the vibration anti-nodes of the longitudinal vibration, is positioned at a connecting position of the proximal side transmitting member 22 and the distal side transmitting member 8 (distal end of the proximal side transmitting member 22). In a state where the vibration transmitting unit 20 performs longitudinal vibration at a frequency in the predetermined frequency range $\Delta f$ (between Frmin and Frmax), the vibration anti-node A2 is positioned at the connecting position of the proximal side transmitting member 22 and the distal side transmitting member 8, or in the vicinity thereof.

In a state where the vibration transmitting unit 20 vibrates at the standard resonance frequency Frref, a vibration node N2 (shown as N2ref in FIG. 3), which is one of the vibration nodes of the longitudinal vibration, is positioned at the cross-sectional reduction portion 45, in a state where the vibration transmitting unit 20 performs longitudinal vibration at a frequency in the predetermined frequency range $\Delta f$ (between Frmin and Frmax), the vibration node N2 is positioned at the cross-sectional reduction portion 45, or in the vicinity thereof. Therefore, in a state where the vibration transmitting unit 20 performs longitudinal vibration at a frequency in the predetermined frequency range $\Delta f$, all of the vibration anti-nodes A1 to A4 of the longitudinal vibration are positioned away from the cross-sectional reduction portion 45 in the direction parallel to the longitudinal axis C. In the present embodiment, the vibration node N2 is a vibration node positioned to the distal side from the vibration node N1 by a half-wavelength $\lambda/2$ of the longitudinal vibration. Since vibration anti-nodes A1 to A4 at which stress caused by vibration becomes zero are not positioned at the cross-sectional reduction portion 45, stress caused by vibration acts on the cross-sectional reduction portion 45 at which the cross-sectional area perpendicular to the longitudinal axis C decreases towards the distal side. Accordingly, the cross-sectional reduction portion 45 increases the amplitude of the longitudinal vibration. Particularly, since the vibration node N2, at which the stress caused by vibration is locally maximized, is positioned at the cross-sectional reduction portion 45 or in the vicinity thereof, the rate of enlargement of the amplitude at the cross-sectional reduction portion 45 increases, and the transformation ratio departs from one.

In a state where the vibration transmitting unit 20 vibrates at the standard resonance frequency Frref, a vibration node N3 (shown as N3ref in FIG. 3), which is one of the vibration nodes of the longitudinal vibration, is positioned at the cross-sectional reduction portion 47. In a state where the vibration transmitting unit 20 performs longitudinal vibration at a frequency in the predetermined frequency range Δf (between Frmin and Frmax), the vibration node N3 is positioned at the cross-sectional reduction portion 47, or in the vicinity thereof. Therefore, in a state where the vibration transmitting unit 20 performs longitudinal vibration at a frequency in the predetermined frequency range Δf, all of the vibration anti-nodes A1 to A4 of the longitudinal vibration are positioned away from the cross-sectional reduction portion 47 in the direction parallel to the longitudinal axis C. In the present embodiment, the vibration node N3 is a vibration node positioned to the distal side from the vibration node N2 by a half-wavelength λ/2 of the longitudinal vibration. Since the vibration anti-nodes A1 to A4, at which the stress caused by vibration becomes zero, are not positioned at the cross-sectional reduction portion 7, the stress caused by the vibration acts on the cross-sectional reduction portion 47 at which the cross sectional area perpendicular to the longitudinal axis C decreases towards the distal side. Accordingly, the cross-sectional reduction portion 47 increases the amplitude of the longitudinal vibration. Particularly, since the vibration node N3, at which the stress caused by vibration is locally maximized, is positioned at the cross-sectional reduction portion 47 or in the vicinity thereof, the rate of enlargement of the amplitude at the cross-sectional reduction portion 47 increases, and the transformation ratio departs from one.

In a state where the vibration transmitting unit 20 (extending portion 31) vibrates at a frequency in the predetermined frequency range Δf (between Frmin and Frmax) including the standard resonance frequency Fr, the standard vibration anti-node A3 (shown as A3ref in FIG. 3), which is one of the vibration anti-nodes, is positioned at the third component 37. In the present embodiment, the vibration node N2 becomes a vibration node that is positioned to the proximal side from the standard anti-node A3 by a quarter wavelength λ/4 (shown as λref/4 in FIG. 3), and the vibration node N3 becomes a vibration node that is positioned to the distal side from the standard anti-node A3 by a quarter wavelength λ/4.

Figure 4:
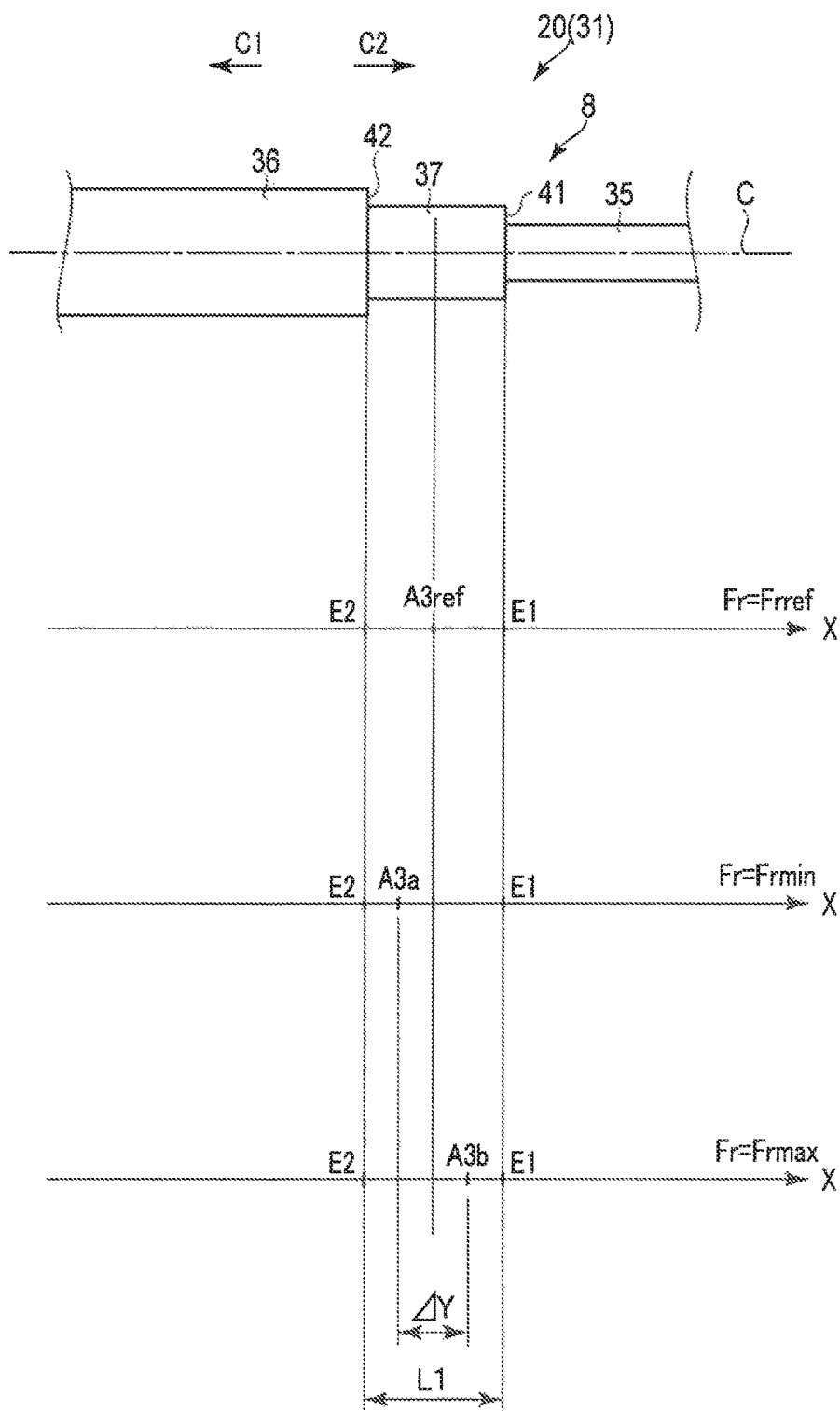
FIG. 4 is a schematic view explaining the change in position of a standard vibration anti-node in a direction parallel to a longitudinal axis, in a state where the vibration transmitting unit according to the first embodiment vibrates in a predetermined frequency range.

FIG. 4 is a diagram explaining the change in position of the standard vibration anti-node A3 in a direction parallel to the longitudinal axis C, in a state where the vibration transmitting unit 20 vibrates in the predetermined frequency range Δf. FIG. 4 shows positions (X) of the standard vibration anti-node A3 in the direction parallel to the longitudinal axis C in a state where the vibration transmitting unit 20 vibrates at each of the standard resonance frequency Frref, the minimum resonance frequency Frmin, and the maximum resonance frequency Frmax. As shown in FIG. 4, in a state where the vibration transmitting unit 20 (extending portion 31) vibrates at the standard resonance frequency Frref, the standard vibration anti-node A3ref is positioned at an approximately intermediate position between the distal end and the proximal end of the third component 37.

When the resonance frequency Fr decreases from the standard resonance frequency Frref to a certain frequency that is smaller than the standard resonance frequency Frref, the wavelength λ of the longitudinal vibration increases. Accordingly, when the resonance frequency Fr decreases from the standard resonance frequency Frref, in comparison to a state in which the vibration transmitting unit 20 vibrates at the standard resonance frequency Frref, the standard vibration anti-node A3 is positioned more distally. In a state where the vibration transmitting unit 20 vibrates at the minimum resonance frequency Frmin of the predetermined frequency range Δf, a standard vibration anti-node A3a is positioned at the most distal position. However, even in a state where the vibration transmitting unit 20 vibrates at the minimum resonance frequency Frmin, the position of the standard vibration anti-node A3a coincides with the distal end of the third component 37 proximal end 52 of the second component 36), or is positioned on the proximal side with respect to the distal end of the third component 37 in the direction parallel to the longitudinal axis C.

On the other hand, when the resonance frequency Fr increases from the standard resonance frequency Frref to a certain frequency that is larger than the standard resonance frequency Frref, the wavelength λ of the longitudinal vibration decreases. Accordingly, when the resonance frequency Fr increases from the standard resonance frequency Frref, in comparison to a state in which the vibration transmitting unit 20 vibrates at the standard resonance frequency Frref, the standard vibration anti-node A3 is positioned more proximally. In a state where the vibration transmitting unit 20 vibrates at the maximum resonance frequency Frmax of the predetermined frequency range Δf, a standard vibration anti-node A3b is positioned at the most proximal position. However, even in a state where the vibration transmitting unit 20 vibrates at the maximum resonance frequency Frmax, the position of the standard vibration anti-node A3b coincides with the proximal end of the third component 37 (a distal end E1 of the first component 35), or is positioned on the distal side with respect to the proximal end of the third component 37 in the direction parallel to the longitudinal axis C.

Accordingly, in a state where the vibration transmitting unit 20 vibrates at a frequency in the predetermined frequency range Δf, the standard vibration anti-node A3 is positioned at the third component 37 (in the present embodiment, a range from the distal end E1 of the first component 35 to the proximal end 32 of the second component 36 in the direction parallel to the longitudinal axis C). Therefore, a standard fluctuation width ΔY, which is a fluctuation width of the standard vibration anti-node A3 in the direction parallel to the longitudinal axis C when the resonance frequency Fr of the vibration transmitting unit 20 changes in the predetermined frequency range Δf, becomes a magnitude equal to or smaller than the extending dimension L1 of the third component 37 in the direction parallel to the longitudinal axis C. Here, the standard fluctuation width ΔY of the standard vibration anti-node A3 in the predetermined frequency range Δf is a distance between a position of the standard vibration anti-node A3a at the minimum resonance frequency Frmin and a position of the standard vibration anti-node A3b at the maximum resonance frequency Frmax in the direction parallel to the longitudinal axis C. In a certain example, the vibration transmitting unit 20 vibrates at a frequency in the predetermined frequency range Δf between 46 kHz and 48 kHz in which the standard resonance frequency Frref becomes 47 kHz. In this case, the standard fluctuation width ΔY of the standard vibration anti-node A3 when vibrating in the predetermined frequency range Δf becomes approximately 2 mm, and the extending dimension L1 of the third component 37 becomes equal to or more than 2 mm. In another example, the vibration transmitting unit 20 vibrates at a frequency in the predetermined frequency range Δf between 46.5 kHz and 47.5 kHz in which the standard resonance frequency Frref becomes 47 kHz. In this case, the standard fluctuation width ΔY of the standard vibration anti-node A3 when vibrating in the predetermined frequency range Δf becomes approximately 1 mm, and the extending dimension L1 of the third component 37 becomes equal to or more than 1 mm.

Since the position of the standard vibration anti-node A3 changes in response to the resonance frequency Fr in the manner mentioned above, in the present embodiment, when the resonance frequency Fr decreases from the standard resonance frequency Frref, in comparison to a state in which the vibration transmitting unit 20 vibrates at the standard resonance frequency Frref, the standard vibration anti-node A3 becomes distant from the cross-sectional increasing portion (proximal side cross-sectional increasing portion) 41. Therefore, when the resonance frequency Fr decreases from the standard resonance frequency Frref, in comparison to a state in which the vibration transmitting unit 20 vibrates at the standard resonance frequency Frref, the stress caused by the vibration at the cross-sectional increasing portion 41 increases, the rate of reduction of the amplitude of the vibration at the cross-sectional increasing portion 41 increases, and the transformation ratio departs from one. However, when the resonance frequency Fr decreases from the standard resonance frequency Frref, in comparison to a state in which the vibration transmitting unit 20 vibrates at the standard resonance frequency Frref, the standard vibration anti-node A3 comes closer to the cross-sectional increasing portion (distal side cross-sectional increasing portion) 42. Therefore, when the resonance frequency Fr decreases from the standard resonance frequency Frref, in comparison to a state in which the vibration transmitting unit 20 vibrates at the standard resonance frequency Frref, the stress caused by the vibration at the cross-sectional increasing portion 42 decreases, the rate of reduction of the amplitude of the vibration at the cross-sectional increasing, portion 42 decreases, and the transformation ratio comes close to one.

As mentioned above, when the resonance frequency Fr decreases from the standard resonance frequency Frref, although the rate of reduction (amount of change) of the amplitude of the vibration at the cross-sectional increasing portion 41 increases, the rate of reduction (amount of change) of the amplitude of the vibration at the cross-sectional increasing portion 42 decreases. Therefore, even if the resonance frequency Fr decreases from the standard resonance frequency Frref, the transformation ratio (rate of reduction) of the amplitude of the longitudinal vibration at the second component 36 (distal side of the cross-sectional increasing portion 12) to the amplitude of the longitudinal vibration at the first component 35 (proximal side of the cross-sectional increasing portion 41) hardly changes, or changes less from a state in which the vibration transmitting unit 20 vibrates at the standard resonance frequency Frref.

In the present embodiment, when the resonance frequency Fr increases from the standard resonance frequency Frref, in comparison to a state in which the vibration transmitting unit 20 vibrates at the standard resonance frequency Frref, the standard vibration anti-node A3 comes closer to the cross-sectional increasing portion (proximal side cross-sectional increasing portion) 41. Therefore, when the resonance frequency Fr increases from the standard resonance frequency Frref, in comparison to a state in which the vibration transmitting unit 20 vibrates at the standard resonance frequency Frref, the stress caused by the vibration at the cross-sectional increasing portion 41 decreases, the rate of reduction of the amplitude of the vibration at the cross-sectional increasing portion 41 decreases, and the transformation ratio comes close to one. However, when the resonance frequency Fr increases from the standard resonance frequency Frref, in comparison to a state in which the vibration transmitting unit 20 vibrates at the standard resonance frequency Frref, the standard vibration anti-node A3 becomes distant from the cross-sectional increasing portion (distal side cross-sectional increasing portion) 42. Therefore, when the resonance frequency Fr increases from the standard resonance frequency Frref, in comparison to a state in which the vibration transmitting unit 20 vibrates at the standard resonance frequency Frref, the stress caused by the vibration at the cross-sectional increasing portion 42 increases, the rate of reduction of the amplitude of the vibration at the cross-sectional increasing portion 42 increases, and the transformation ratio departs from one.

As mentioned above, when the resonance frequency Fr increases from the standard resonance frequency Frref, although the rate of reduction (amount of change) of the amplitude of the vibration at the cross-sectional increasing portion 41 decreases, the rate of reduction (amount of change) of the amplitude of the vibration at the cross-sectional increasing portion 42 increases. Therefore, even if the resonance frequency Fr increases from the standard resonance frequency Frref, the transformation ratio (rate of reduction) of the amplitude of the longitudinal vibration at the second component 36 (distal side of the cross-sectional increasing portion 42) to the amplitude of the longitudinal vibration at the first component 35 (proximal side of the cross-sectional increasing portion 41) hardly changes, or changes less from a state in which the vibration transmitting unit 20 vibrates at the standard resonance frequency Frref.

Accordingly, in the vibration transmitting unit 20 of the present embodiment, even if the resonance frequency Fr is variable in the predetermined frequency range Δf between the minimum resonance frequency Frmin and the maximum resonance frequency Frmax, the transformation ratio (rate of reduction) of the amplitude of the longitudinal vibration at the second component 36 (distal side of the cross-sectional increasing portion 42) to the amplitude of the longitudinal vibration at the first component 35 (proximal side of the cross-sectional increasing portion 41) hardly changes, or has small variability. That is, even if the resonance frequency Fr is variable, the variability of the transformation ratio (rate of reduction) of the amplitude of the vibration while the ultrasonic vibration is transmitted from the first component 35 to the second component 36 through the cross-sectional increasing portion 41, the third component 37, and the cross sectional increasing portion 42 of the vibration transmitting unit 20 can be reduced. Therefore, the variability of the amplitude of the ultrasonic vibration transmitted through the cross-sectional increasing portions 41 and 42 can be reduced in the treatment portion 17 (a region on the distal side with respect to the cross-sectional increasing portion 42). By reducing the variability of the amplitude at the treatment portion 17, the treatment portion 17 can steadily perform a treatment using ultrasonic vibration.

By making the third cross-sectional area S3 of the third component 37 identical to an average value of the first cross-sectional area S1 of the first component 35 and the second cross-sectional area S2 of the second component 36, the variability in the transformation ratio (rate of reduction) of the amplitude of the vibration while the ultrasonic vibration is transmitted from the first component 35 to the second component 36 through the the cross-sectional increasing portion 41, the third component 37, and the cross-sectional increasing portion 42 can be further reduced. Accordingly, the variability of the amplitude of the ultrasonic vibration transmitted through the cross-sectional increasing portions 41 and 42 can be further reduced in the treatment portion 17 (a region on the distal side with respect to the cross-sectional increasing portion 42).

As shown in FIG. 3 and FIG. 4, in a state where the vibration transmitting unit 20 (extending portion 31) vibrates at a frequency in the predetermined frequency range Δf (between the minimum resonance frequency Frmin and the maximum resonance frequency Frmax), the vibration node N2 positioned to the proximal side from the standard vibration anti-node A3 by a quarter wavelength λ/4 (shown as λref/4 in FIG. 3) is positioned on the proximal side with respect to the distal end E1 of the first component 35 (the proximal end of the third component 37 in the present embodiment). In a state where the vibration transmitting unit 20 (extending portion 31) vibrates at a frequency in the predetermined frequency range Δf, the vibration node N3 positioned to the distal side from the standard vibration anti-node A3 by a quarter wavelength λ/4 (shown as λref/4 in FIG. 3) is positioned on the distal side with respect to the distal end E2 of the second component 36 (the distal end of the third component 37 in the present embodiment). Therefore, in a state where the vibration transmitting unit 20 vibrates at a frequency in the predetermined frequency range Δf, a half-wavelength λ/2 of the longitudinal vibration becomes larger than the extending dimension L1 of the third component 37 in the direction parallel to the longitudinal axis C. All of the vibration nodes (N1 to N3) of the longitudinal vibration, in which stress caused by vibration is locally maximized, are positioned away from the third component 37 in the direction parallel to the longitudinal axis C.

In the present embodiment, in a state where the vibration transmitting unit 20 (extending portion 31) vibrates at a frequency in the predetermined frequency range Δf, a quarter wavelength λ/4 of the longitudinal vibration becomes larger than the extending dimension L1 of the third component 37 in the direction parallel to the longitudinal axis C. In a state where the vibration transmitting unit 20 vibrates at a frequency in the predetermined frequency range Δf, a position Q1 (shown as Q1ref in FIG. 3), which is located to the proximal side from the standard vibration anti-node A3 by a sixteenth of a wavelength λ/16 (shown as λref/16 in FIG. 3), is positioned on the proximal side with respect to the distal end E1 of first component 35 (the proximal end of the third component 37 in the present embodiment). Therefore, in a state where the vibration transmitting unit 20 (extending portion 31) vibrates at a frequency in the predetermined frequency range Δf, a distance between the standard vibration anti-node A3, in which the stress caused by vibration is zero, and the cross-sectional increasing portion 41 (distal end E1 of the first component 35) becomes zero or small. Accordingly, at the cross-sectional increasing portion 41, the stress caused by vibration becomes zero or small, and the amplitude of the vibration hardly decrease.

In a state where the vibration transmitting unit 20 (extending portion 31) vibrates at a frequency in the predetermined frequency range Δf, a position Q2 (shown as Q2ref in FIG. 3), which is located to the distal side from the standard vibration an A3 by a sixteenth of a wavelength λ/16 (shown as λref/16 in FIG. 3), is positioned on the distal side with respect to the proximal end 22 of second component 36 (the distal end of the third. component 37 in. the present embodiment). Therefore, in a state where the vibration transmitting unit 20 (extending portion 31) vibrates at a frequency in the predetermined frequency range Δf, a distance between the standard vibration anti-node A3, in which the stress caused by vibration is zero, and the cross-sectional increasing portion 42 (proximal end E2 of the second component becomes zero or small. Accordingly, at the cross-sectional increasing portion 42, the stress caused by vibration becomes zero or small, and the amplitude of the vibration. hardly decreases.

Accordingly, in the present embodiment, the amplitude of the longitudinal vibration that is enlarged at the cross-sectional reduction portions 32 and 45 hardly decreases at the cross-sectional increasing portions 41 and 42. The amplitude of the longitudinal vibration is further enlarged at the cross-sectional reduction portion 47, and the ultrasonic vibration is transmitted to the treatment portion 17. Therefore, it is possible to realize an amplitude of a longitudinal vibration having a magnitude suitable for treatment at the treatment portion 17, which would improve treatment capability.

In the present embodiment, the cross-sectional increasing portions 41 and 42, which hardly reduce the amplitude of the longitudinal vibration in a state where the vibration transmitting unit 20 vibrates at a frequency in the predetermined frequency range Δf, are provided between the cross-sectional reduction portion 45 and the cross-sectional reduction portion 47 in the direction parallel to the longitudinal axis C. Therefore, without having to make (without thickening) the diameter of a region on the proximal side larger with respect to the cross-sectional reduction portion (proximal side cross sectional reduction portion) 45, the amplitude of the longitudinal vibration is appropriately enlarged. By not forming the region on the proximal side of the cross-sectional reduction portion 45 to have a larger diameter, a region of the ultrasonic treatment instrument 2 to be inserted into a body (the sheath 6 and the distal side transmitting member 8) can be formed in a small diameter (thinly) across the entire length in the direction parallel to the longitudinal axis C. The region of the ultrasonic treatment instrument 2 to be inserted into a body having a small diameter improves the insertability of the jaw 7 and the treatment portion 17 into the body upon treatment.

MODIFIED EXAMPLE

Figure 5:
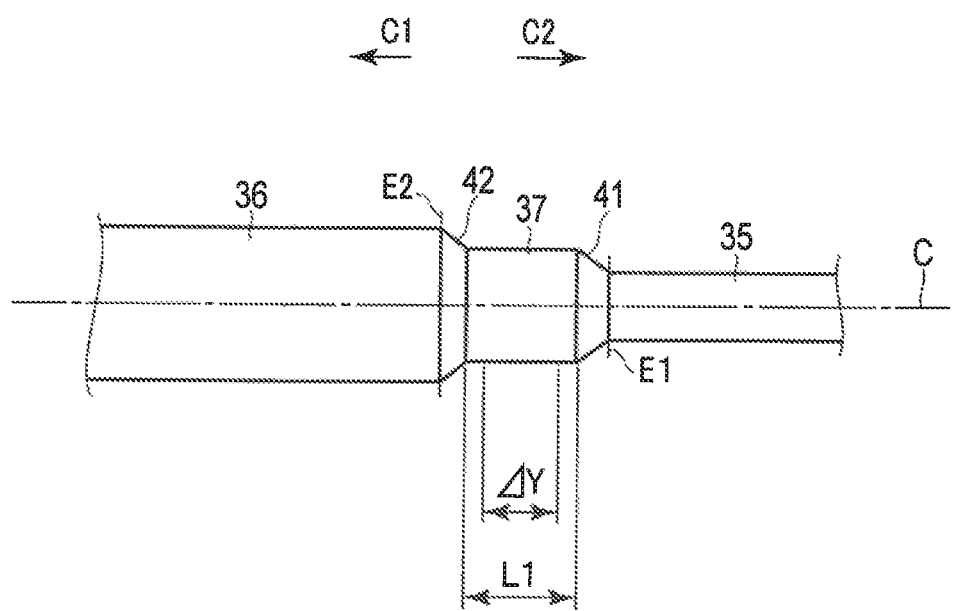
FIG. 5 is a schematic view showing a configuration of a third component and the vicinity thereof of a vibration transmitting unit according to a first modification.

In a first embodiment, the cross-sectional increasing portion 41 between the first component 35 and the third component 37, and the cross-sectional increasing portion 42 between the third component 37 and the second component 36 are formed stepwise. However, this is not restrictive. For example, as in the first modification shown in FIG. 5, each of the cross-sectional increasing portions 41 and 42 may be formed in a tapered shape so that the cross-sectional area perpendicular to the longitudinal axis C gradually increases towards the distal side. In the present modification, the cross-sectional increasing portion 41 extends between the distal end E1 of the first component 35 and the proximal end of the third component 37 along the longitudinal axis C, and the cross-sectional increasing portion 42 extends between the distal end of the third component 37 and the proximal end E2 of the second component 36 along the longitudinal axis C. Accordingly, the proximal end of the third component 37 is continuous with the distal end E1 of the cross-sectional increasing portion 41, and the distal end of the third component 37 is continuous with the proximal end of she cross-sectional increasing portion 42.

Also, in the present modification, in a state where the vibration transmitting unit 20 (extending portion 31) vibrates at a frequency in the predetermined frequency range Δf (between the minimum resonance frequency Frmin and the maximum resonance frequency Frmax), the standard vibration anti-node A3 which is one of the vibration anti-nodes is positioned in the third component 37. That is, the standard vibration anti-node A3 is positioned across a range from the proximal end of the third component 37 (the distal end of the cross-sectional increasing portion 41) to the distal end of the third component 37 (proximal end of the cross-sectional increasing portion 42). Accordingly, also in the present modification, the standard fluctuation width ΔY, which is a fluctuation width of the standard vibration anti-node A3 in the direction parallel to the longitudinal axis C when the resonance frequency Fr of the vibration transmitting unit 20 changes in the predetermined frequency range Δf, becomes a magnitude equal to or smaller than the extending dimension L1 of the third component 37 in the direction parallel to the longitudinal axis C. The extending dimension L1 is a dimension from the proximal end of the third component 37 (the distal end of the cross-sectional increasing portion 41) to the distal end of the third component 37 (the proximal end of the cross-sectional increasing portion 42), and does not include dimensions of the cross-sectional increasing portion 41 (a portion extending in a tapered shape) and the cross-sectional increasing portion 42 (a portion extending in a tapered shape).

Also, in the present modification, in a state where the vibration transmitting unit 20 vibrates at a frequency the predetermined frequency range Δf, all of the vibration nodes N1 to N3 are positioned away from the third component 37 in the direction parallel to the longitudinal axis C. Also, in the present modification, in a state where the vibration transmitting unit 20 vibrates at a frequency in the predetermined frequency range Δf, the position Q1, which is located to the proximal side from the standard vibration anti-node A3 by a sixteenth of a wavelength λ/16 is positioned on the proximal side with respect to the distal end E1 of first component 35, and the position Q2, which is located to the distal side from the standard vibration anti-node A3 by a sixteenth of a wavelength λ/16, is positioned on the distal side with respect to the distal end E2 of second component 36. Therefore, also in the present modification, the distance from the standard vibration anti-node A3 to each of the cross-sectional increasing portions 41 and 42 becomes zero or small. Accordingly, in each of the cross-sectional increasing portions 41 and 42, the stress caused by the vibration becomes zero or decreases, and the amplitude of the vibration hardly decreases.

In the above-mentioned embodiment, etc. the cross-sectional reduction portions 32, 45, and 47 are provided on the vibration transmitting unit 20. However, this is not restrictive. For example, in a certain modification, the cross-sectional reduction portion 45 and the relay portion (proximal side relay portion) 46 are not provided, and the first component 35 is continuous between the cross-sectional reduction portion 32 and the cross-sectional increasing portion 41 in the direction parallel to the longitudinal axis C. Also, in the present modification, the first component 35 has a first cross-sectional area S1 on the cross-section perpendicular to the longitudinal axis C. Therefore, in the present modification, at the cross-sectional reduction portion 32 of the proximal side transmitting member 22, a cross-sectional area perpendicular to the longitudinal axis C is reduced down to the first cross-sectional area S1 towards the distal side.

In a certain modification, in addition to transmitting the ultrasonic vibration to the treatment portion 17, a high frequency electric power (high frequency electric energy) is supplied to the treatment portion 17 and to the jaw 7. In the above manner, a high frequency current flows through the treated target that is grasped between the treatment portion 17 and the jaw 7. As the high-frequency current flows through, the treated target is denatured, and coagulation is accelerated.

In a certain modified example, the jaw 7 does not have to be provided. In this case, the treatment portion 17 provided in the distal portion of the vibration transmitting unit 20 is formed in a shape of a hook or a spatula, etc. For example, in the case where the treatment portion 17 is formed in the shape of a hook, the treated target is resected by the ultrasonic vibration causing the vibration transmitting unit 20 to perform longitudinal vibration in a state where the hook hooks the treated target. When doing so, a high-frequency electric power may be simultaneously supplied to the treatment portion 17 to flow a high-frequency current to the treated target.

In the above-mentioned embodiment, etc. in the vibration transmitting unit (20), the extending portion (31) extends along the longitudinal axis (C), and is capable of transmitting ultrasonic vibration from the proximal side (C1) to the distal side (C2). The extending portion (31) includes the first component (35) having the first cross-sectional area (S1) in a cross-section perpendicular to the longitudinal axis (C), and the second component (36) provided on the distal side with respect to the first component (35) and having the second cross-sectional area (S2) that is larger than the first cross-sectional area (S1) in a cross-section perpendicular to the longitudinal axis (C). Furthermore, the extending portion (31) provided with, between the first component (35) and the second component (36), the third component (37) which has the third cross-sectional area (S3) that is larger than the first cross-sectional area (S1) and is smaller than the second cross-sectional area (S2) in the cross-section perpendicular to the longitudinal axis (C), and at which the standard vibration anti-node (A3), being one of the vibration anti-nodes, is positioned by the ultrasonic vibration causing the extending portion (31) to vibrate at a frequency in the predetermined frequency range Δf.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:
1. A vibration transmitting unit comprising:
an extending portion which extends along a longitudinal axis, and which is capable of transmitting ultrasonic vibration from a proximal side to a distal side;
a first component which is provided in the extending portion, and which has a first cross-sectional area in a cross-section perpendicular to the longitudinal axis;
a second component which is provided on the distal side with respect to the first component in the extending portion, and which has a second cross-sectional area, which is larger than the first cross-sectional area, in a cross-section perpendicular to the longitudinal axis;
a third component which is provided between the first component and the second component in the extending portion, and which has a third cross-sectional area, which is larger than the first cross-sectional area and is smaller than the second cross-sectional area, in a cross-section perpendicular to the longitudinal axis, a standard vibration anti-node, which is one of vibration anti-nodes, being positioned at the third component by the ultrasonic vibration causing the extending portion to vibrate at a frequency in a predetermined frequency range, the third cross-sectional area being constant in an entirety of the third component in a direction parallel to the longitudinal axis;

a first cross-sectional increasing portion which is provided at a boundary between the first component and the third component, and an entirety of the first cross-sectional increasing portion being perpendicular to the longitudinal axis; and a second cross-sectional increasing portion which is provided at a boundary between the second component and the third component, and an entirety of the second cross-sectional increasing portion being perpendicular to the longitudinal axis, wherein the third component, in which a cross-sectional area perpendicular to the longitudinal axis is kept constant at the third cross-sectional area in an entire length in the direction parallel to the longitudinal axis, continuously extends from the first cross-sectional increasing portion to the second cross-sectional increasing portion, the extending portion includes a first cross-sectional reduction portion which is provided on the proximal side with respect to the first component, and which reduces a cross-sectional area perpendicular to the longitudinal axis towards the distal side to the first cross-sectional area of the first component, and in a state where the extending portion vibrates at a frequency in the predetermined frequency range, all of the vibration anti-nodes are positioned away from the first cross-sectional reduction portion in the direction parallel to the longitudinal axis.

2. The vibration transmitting unit according to claim 1, wherein, in a state where the extending portion vibrates at a frequency in the predetermined frequency range, a half-wavelength of vibration is larger than an extending dimension of the third component in the direction parallel to the longitudinal axis.

3. The vibration transmitting unit according to claim 2, wherein in a state where the extending portion vibrates at a frequency in the predetermined frequency range:

a first vibration node, which is positioned to the proximal side from the standard vibration anti-node by a ¼ wavelength of the vibration, is positioned on the proximal side with respect to a distal end of the first component, and a second vibration node, which is positioned to the distal side from the standard vibration anti-node by a ¼ wavelength of the vibration, is positioned on the distal side with respect to a proximal end of the second component.

4. The vibration transmitting unit according to claim 3, wherein a position, which is located to the proximal side from the standard vibration anti-node by a 1/16 wavelength, is positioned on the proximal side with respect to the distal end of the first component, and a position, which is located to the distal side from the standard vibration anti-node by a 1/16 wavelength, is positioned on the distal side with respect to a proximal end of the first component.

5. The vibration transmitting unit according to claim 1, wherein a standard fluctuation width, which is a fluctuation width of the standard vibration anti-node in the direction parallel to the longitudinal axis when a resonance frequency is changed in the predetermined frequency range, is equal to or less than an extending dimension of the third component in the direction parallel to the longitudinal axis.

6. The vibration transmitting unit according to claim 1, wherein the third cross-sectional area of the third component is identical to an average value of the first cross-sectional area of the first component and the second cross-sectional area of the second component.

7. The vibration transmitting unit according to claim 1, wherein the extending portion includes a second cross-sectional reduction portion which is provided on the distal side with respect to the second component, and which reduces a cross-sectional area perpendicular to the longitudinal axis from the second cross-sectional area of the second component towards the distal side, and in a state where the extending portion vibrates at a frequency in the predetermined frequency range, all of the vibration anti-nodes are positioned away from the second cross-sectional reduction portion in the direction parallel to the longitudinal axis.

8. An ultrasonic treatment instrument comprising:

the vibration transmitting unit according to claim 1;

a vibration generator which generates the ultrasonic vibration to be transmitted to the vibration transmitting unit; and a treatment portion which is provided in the vibration transmitting unit, and which performs treatment using the transmitted ultrasonic vibration.

9. The ultrasonic treatment instrument according to claim 8, wherein all of vibration nodes are positioned away from the third component in the direction parallel to the longitudinal axis.

10. The ultrasonic treatment instrument according to claim 8, wherein an extending dimension of the third component in the direction parallel to the longitudinal axis is smaller than a ¼ wavelength.

11. The ultrasonic treatment instrument according to claim 8, wherein an extending dimension of the third component in the direction parallel to the longitudinal axis is equal to or more than 1 mm.

12. The ultrasonic treatment instrument according to claim 8, wherein an extending dimension of the third component in the direction parallel to the longitudinal axis is equal to or more than 2 mm.

13. The ultrasonic treatment instrument according to claim 8, wherein, in a state where the extending portion vibrates at a frequency in the predetermined frequency range, a half-wavelength of vibration is larger than an extending dimension of the third component in the direction parallel to the longitudinal axis.

14. The ultrasonic treatment instrument according to claim 13, wherein in a state where the extending portion vibrates at a frequency in the predetermined frequency range:

a first vibration node, which is positioned to the proximal side from the standard vibration anti-node by a ¼ wavelength of the vibration, is positioned on the proximal side with respect to a distal end of the first component, and a second vibration node, which is positioned to the distal side from the standard vibration anti-node by a ¼ wavelength of the vibration, is positioned on the distal side with respect to a proximal end of the second component.

15. The ultrasonic treatment instrument according to claim 14, wherein a position, which is located to the proximal side from the standard vibration anti-node by a 1/16 wavelength, is positioned on the proximal side with respect to the distal end of the first component, and a position, which is located to the distal side from the standard vibration anti-node by a $\frac{1}{16}$ wavelength, is positioned on the distal side with respect to the proximal end of the first component.

16. The vibration transmitting unit according to claim 1, wherein an extending dimension of the third component in the direction parallel to the longitudinal axis is larger than a dimension of the first cross-sectional increasing portion in the direction parallel to the longitudinal axis, and the extending dimension of the third component in the direction parallel to the longitudinal axis is larger than a dimension of the second cross-sectional increasing portion in the direction parallel to the longitudinal axis.

17. The vibration transmitting unit according to claim 1, wherein all of vibration nodes are positioned away from the third component in the direction parallel to the longitudinal axis.

18. The vibration transmitting unit according to claim 1, wherein an extending dimension of the third component in the direction parallel to the longitudinal axis is smaller than a $\frac{1}{4}$ wavelength.

19. The vibration transmitting unit according to claim 1, wherein an extending dimension of the third component in the direction parallel to the longitudinal axis is equal to or more than 1 mm.

20. The vibration transmitting unit according to claim 1, wherein an extending dimension of the third component in the direction parallel to the longitudinal axis is equal to or more than 2 mm.

* * * * *